United States Patent [19]

Dutschke

[11] 4,255,703

[45] Mar. 10, 1981

[54] APPARATUS FOR TESTING THE SIZE AND THE SPACINGS OF SILICON CRYSTALS IN AL-SI ALLOYS

[75] Inventor: Wolfgang Dutschke, Leonberg-Eltingen, Fed. Rep. of Germany

[73] Assignee: Fraunhofer-Gesellschaft zur Förderung der angewandten Forschung e.V., München, Fed. Rep. of Germany

[21] Appl. No.: 12,426

[22] Filed: Feb. 15, 1979

[51] Int. Cl.³ .................. G01R 27/02; G01N 27/00
[52] U.S. Cl. .................. 324/71 CP; 324/65 R; 324/65 P; 324/71 R; 324/158 P
[58] Field of Search .......... 324/71 CP, 71 R, 158 P, 324/71 CR, 65 R, 65 P

[56] References Cited

U.S. PATENT DOCUMENTS

| | | | |
|---|---|---|---|
| 2,942,248 | 6/1960 | Huggins | 324/54 X |
| 3,225,296 | 12/1965 | Roth | 324/158 P X |
| 3,247,454 | 4/1966 | Gale et al. | 324/65 P X |

OTHER PUBLICATIONS

Test Probe With Variable Ground & Constant Impedance Capabilities, M. R. Marasch & M. F. McAllister, IBM Technical Disclosure Bulletin, vol. 18, No. 3, Aug. 1975, pp. 699 & 700.
Orbiting Probe: IBM Technical Disclosure Bulletin, vol. 13, No. 7, Dec. 1970, pp. 2113 & 2114, J. W. Wagner & P. M. Young.
Electrical Probe, IBM Technical Disclosure Bulletin, vol. 8, No. 12, May 1966, F. L. Graner & W. Kunzelman, pp. 1722 & 1723.

Primary Examiner—Harold A. Dixon
Attorney, Agent, or Firm—John C. Smith, Jr.

[57] ABSTRACT

An apparatus for testing the size and the spacings of silicon crystals in Al-Si alloys comprises a housing; a horizontal guide accommodated in the housing, and a pointed scanning needle secured by a spring device to the horizontal guide with constant feed. The needle is arranged to scan a surface of a workpiece to be tested with a predetermined force and has applied thereto an electrical voltage which upon contacting an aluminum section of the workpiece transmits a voltage applied to the workpiece to a voltmeter, but partially or entirely interrupts same upon contacting a silicon crystal.

9 Claims, 1 Drawing Figure

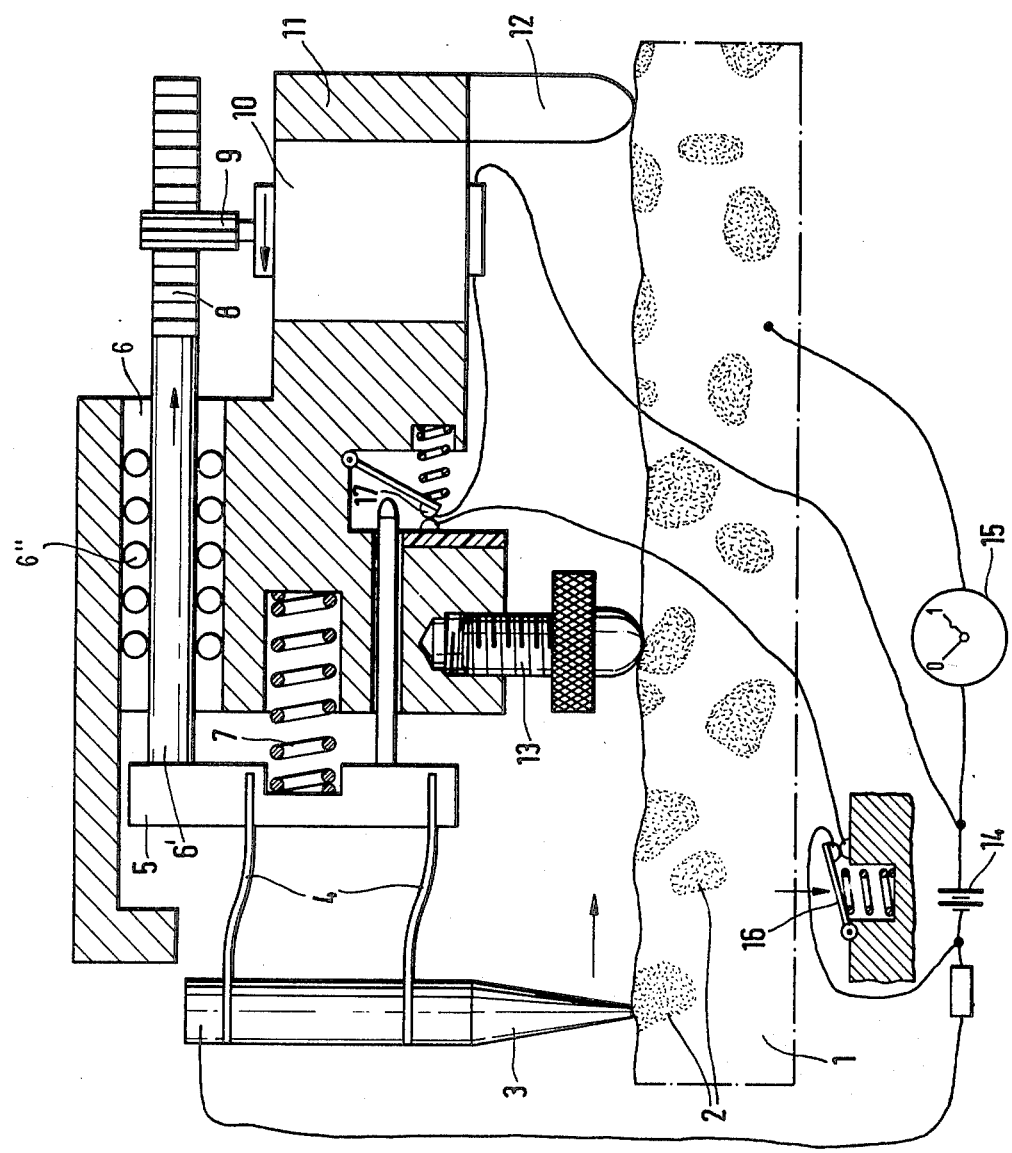

APPARATUS FOR TESTING THE SIZE AND THE SPACINGS OF SILICON CRYSTALS IN AL-SI ALLOYS

BACKGROUND OF THE INVENTION

This invention relates to an apparatus by means of which the position and size of silicon crystals may be determined at machined surfaces of an Al-Si alloy from which e.g. cylinder sleeves or motor blocks for automotive vehicles are made.

The silicon crystals represent supporting points along which the light-metal piston slides. The size and the distribution of these supporting points on the peripheral surface of the cylinder have a decisive effect on the life of the motor and should therefore be tested at each motor block. The metallographic and optical methods used up to now are suited for laboratory measurements, but are too costly and too time-consuming for production. The scanning intersection methods used for surface testing are just as unsuited as light intersection and interference microscopes because the surface structure in the region of the aluminum and in the region of the silicon crystals has no systematic differences which are able to be detected with these methods.

Thus, the appartus known up to now cannot be used for detecting silicon crystals.

SUMMARY OF THE INVENTION

It is the object of the present invention to avoid the above-mentioned disadvantages and to provide a mechanical-electric scanning device which permits to detect the mentioned crystal distribution in a simple and unambiguous manner.

To attain this object the present invention provides an apparatus for testing the size and the spacings of silicon crystals in Al-Si alloys, comprising a housing; a horizontal guide accommodated in the housing, and a pointed scanning needle secured by spring means to the horizontal guide with constant feed, said scanning needle being arranged to scan a surface of a workpiece to be tested with a predetermined force and having applied thereto an electrical voltage which upon contacting an aluminum section of the workpiece transmits a voltage applied to the workpiece to a voltmeter, but partially or entirely interrupts same upon contacting a silicon crystal.

BRIEF DESCRIPTION OF THE DRAWING

An embodiment of the invention will now be described by way of example and with reference to the accompanying drawing, in which the only FIGURE is a longitudinal section of an apparatus according to the invention.

DESCRIPTION OF THE PREFERRED EMBODIMENT

The invention is based on the high electrical conductivity of aluminum and the low conductivity of silicon. The apparatus illustrated in the drawing comprises a housing 11 engaging a surface of a workpiece to be tested through the intermediary of stationary skids 12 and adjustable skids 13. The nature and shape of the skids 12 and 13 depend on the geometrics of the surface of the workpiece. In the housing 11, there is arranged a horizontal guide 6 including bearings 6" with a guide rod 6' including a support 5 on which a rack 8 is provided which is driven by an electric motor 10 via a pinion 9. The electric motor 10 is connected to a voltage source 14 via a switch 16. When the switch 16 is closed, the guide rod 6' moves together with the support 5 of non-conductive material and a leaf-spring parallel guide 4 together with a pointed electrically scanning needle 3 across the surface that is to be tested. The point of the scanning needle is made of a hard and wear-resistant material and has a point angle and a curvature radius correlated to the dimensions of the silicon crystals and the hardness of the aluminum. The scanning needle 3 and the surface to be tested represent a switch, which is rendered conductive with the voltage of the voltage source 14 to a voltmeter 15 or is interrupted. In the drawing, the electrically conductive scanning needle 3 is just resting on an electrically non-conductive silicon crystal 2 which is embedded in the conductive aluminum 1, the battery voltage is interrupted and the voltmeter 15 indicates 0.

In a position of the scanning needle 3 not illustrated in the drawing on the conductive aluminum 1, the circuit is closed, and at the voltmeter 15 a voltage is indicated. In the course of measurement, the signal indicated at the voltmeter 15 continuously varies. At the end of the measurement length, the circuit is interrupted by a limit switch 17 and the guide rod 6' returns into its starting position as a result of the force of a spring 7. By closing the switch 16 a new measurement cycle is initiated.

If instead of the voltmeter 15 a (storage) oscillograph having constant time deviation is provided, the electron beam indicates the sequence of conductive and non-conductive sections of the scanned test surface, and from the number and width of the deflections, the distribution of the silicon crystals in the region of the scanned test surface may be derived. By means of a high-speed recorder, the indicated course may also be recorded. When by time measurements via a gate circuit the duration upon scanning the non-conductive and the conductive sections of the test surface is measured and correlated to the measurement time, a "supporting proportion" may thereby be calculated. By suitable calculation circuits, furthermore parameters of the distribution of the width of silicon crystals may be determined.

The subject matter of the present invention represents testing means of non-destructive material testing which is able to be used in production and which is substantially insensitive to interference parameters in production. The testing time lasts only a few seconds, i.e. it is so short that the machining process need not be interrupted. The described method is suited both for the production of new cylinder tracks and for the repair of used ones, it may therefore be used both by motor manufacturers and by repair shops (cylinder grinding shops).

The invention may be embodied in other specific forms without departing from the spirit or the essential characteristics thereof. The embodiment is therefore to be considered in all respects as illustrative and not restrictive.

What is claimed is:

1. Apparatus for testing the size and spacings of silicon crystals in Al-Si alloys, comprising:
   (a) housing means adapted to be supported on a surface of an article composed of said alloy;
   (b) carrier means mounted on said housing means for movement along a horizontal path relative to said housing means;
   (c) a pointed scanning needle;

(d) means mounting said scanning needle on said carrier means and biasing said scanning needle in the direction of the surface of said article such that with movement of said carrier means along said path the point of said scanning needle contacts the surface of said article with a predetermined force as it moves across said surface;

(e) means for driving said carrier along said path;

(f) a source of electrical current;

(g) voltage indicating means; and (h) circuit means for electrically connecting said article with said scanning needle, said source of electrical current and said voltage indicating means;

(i) whereby the size and spacings of the silicon crystals in said alloy may be determined by the variation of electrical current through said circuit means as indicated by said voltage indicating means during the time period that the point of said scanning needle moves across said surface of said article.

2. Apparatus according to claim 1 wherein said housing means comprises support means for engaging said surface of an article containing said alloy, said support means being adjustable to change the distance between said housing means and the surface of said article to adjust the pressure of the point of said scanning needle against the surface of said article.

3. Apparatus according to claim 2 wherein said support means comprises a plurality of skids, the length of at least one of said skids being adjustable.

4. Apparatus according to claim 1 wherein said housing means includes guide means supporting said carrier means for movement along said horizontal path.

5. Apparatus according to claim 4 wherein said carrier means and driving means comprise a rack and pinion arrangement.

6. Apparatus according to claim 1 wherein said means mounting and biasing said scanning needle comprises spring means extending between said carrier means and said scanning needle for maintaining the point of said scanning needle against said surface.

7. Apparatus according to claim 1 wherein the point of said scanning needle is made of a hard and wear-resistant material, the point angle and curvature radius of said scanning needle being correlated to the dimensions of the silicon crystals and the hardness of the aluminum.

8. Apparatus according to claim 1 wherein said driving means is adapted to drive said carrier means in one direction from a starting position, said apparatus further comprising means adapted to be triggered upon said carrier means moving a predetermined distance in said one direction to return said carrier means to said starting position.

9. Apparatus according to claim 1 wherein at least a portion of said carriers means is electrically non-conductive.

* * * * *